United States Patent [19]

Hunt

[11] Patent Number: 4,463,184

[45] Date of Patent: Jul. 31, 1984

[54] PROCESS FOR THE PREPARATION OF CARBOFURAN

[75] Inventor: David A. Hunt, Durham, N.C.

[73] Assignee: Union Carbide Corporation, Danbury, Conn.

[21] Appl. No.: 429,199

[22] Filed: Sep. 30, 1982

Related U.S. Application Data

[63] Continuation-in-part of Ser. No. 289,361, Jul. 31, 1981, abandoned.

[51] Int. Cl.$^3$ .................. C07D 307/86; C07D 49/603
[52] U.S. Cl. ..................... 549/470; 549/462; 568/377
[58] Field of Search ................. 549/462, 470; 568/377

[56] References Cited

U.S. PATENT DOCUMENTS 3,320,286  5/1967  Franko-Filipasic .............. 260/346.2

FOREIGN PATENT DOCUMENTS 1258554 12/1971 United Kingdom .

OTHER PUBLICATIONS

Tamura et al., Chemical and Pharmaceutical Bulletin, vol. 19(3), pp. 571–575 (1971).

Primary Examiner—John M. Ford
Assistant Examiner—Bernard Dentz
Attorney, Agent, or Firm—W. R. Moran; J. A. Shedden

[57] ABSTRACT

A novel process is provided for the preparation of carbofuran and certain intermediate products. 1,2-Cyclohexanedione is alkylated with a beta-methallyl compound and the resulting product subjected to a Claisen rearrangement/aromatization to provide the carbofuran phenol. Reaction of the phenol with methyl isocyanate converts the phenol to the desired carbofuran.

19 Claims, No Drawings

PROCESS FOR THE PREPARATION OF CARBOFURAN

This application is a continuation-in-part of application Ser. No. 289,361 filed July 31, 1981 now abandoned.

FIELD OF THE INVENTION

This invention relates, in general, to an improved process for the preparation of carbofuran and to certain intermediate products. In one aspect this invention is directed to a simple, two step process for preparing carbofuran phenol from relatively inexpensive materials. In a further aspect, this invention involves the alkylation of 1,2-cyclohexanedione followed by either a catalytic or non-catalytic Claisen rearrangement/aromatization.

BACKGROUND OF THE INVENTION

Carbofuran is a systemic insecticide, acaricide, and nematicide currently manufactured and used in the United States and throughout the world. The product can be produced by the sequential conversion of o-nitrophenol to 2-beta-methallyloxynitrobenzene, 2,3-dihydro-2,2-dimethyl-7-nitrobenzo-furan, 2,3-dihydro-2,2-dimethyl-7-benzofuranol, and finally 2,3-dihydro-2,2-dimethyl-7-benzofuranyl-N-methyl carbamate as described in U.S. Pat. No. 3,320,286 which issued to FMC Corporation on May 16, 1967. However, the major disadvantages of the process are the expense and difficulty encountered in the preparation.

The most current procedures for the preparation of carbofuran as disclosed in the patent literature involve the alkylation of a 2-substituted phenol or phenol per se with beta-methallyl chloride, followed by a Claisen rearrangement. The product, the 7-substituted-2,3-dihydro-2,2-dimethylbenzofuran, is then subjected to further transformations on the functional group at the 7-position in order to produce the desired benzofuranol. One process currently believed to be in use for the preparation of carbofuran is described in U.S. Pat. No. 3,320,286 and involves five distinct steps.

The process which involves the conversion of the aminobenzofuran to the benzofuranol via the diazonium salt is hazardous and requires special care in handling due to the potentially explosive nature of diazo salts. Thus, prior to the present invention, there was no simple process which utilized relatively inexpensive materials and avoided the hazards associated with diazonium salts.

Accordingly, one or more of the following objects can be achieved by the practice of this invention. It is an object of this invention to provide an improved process for the preparation of carbofuran and certain novel intermediate products. Another object of this invention is to provide a process which is simple and employs readily available and inexpensive starting materials. A further object is to provide a process which utilizes 1,2-cyclohexanedione as the starting material. Another object of the invention is to provide a simple two step process for the preparation of carbofuran phenol. These and other objects will readily become apparent to those skilled in the art in the light of the teachings hereinafter set forth.

SUMMARY OF THE INVENTION

The invention relates, in general, to an improved process for the preparation of carbofuran and to certain intermediate products. The process comprises alkylating 1,2-cyclohexanedione with a beta-methallyl compound and subjecting the resulting product to a Claisen rearrangement/aromatization to provide carbofuran phenol. Reaction of the phenol with methyl isocyanate gives the carbofuran.

DETAILED DESCRIPTION OF THE INVENTION

As indicated above, the invention is directed to an improved process for the preparation of carbofuran and to certain intermediate products. In the preferred route, 1,2-cyclohexanedione is O-alkylated with beta-methallyl chloride via base catalysis or O-alkylated with beta-methallyl alcohol via acid catalysis to give the corresponding beta-methallyldiosphenol III.

The process can be outlined as follows:

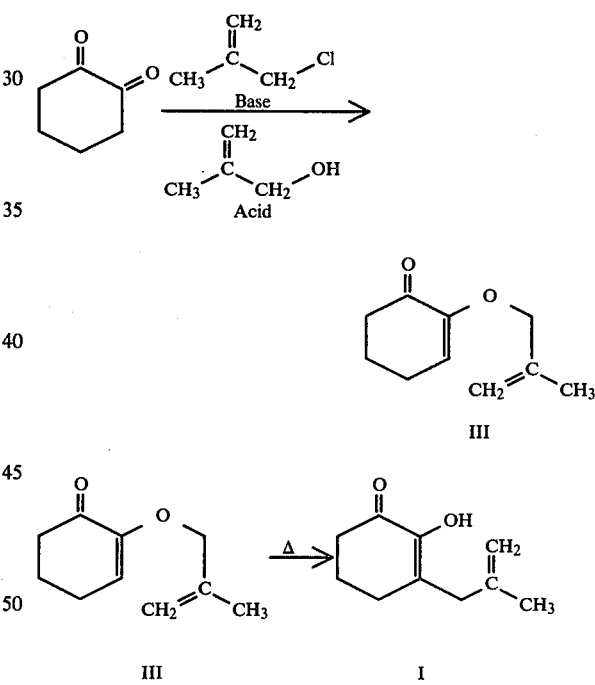

The key step in the process is the rearrangement of the diosphenol III to the 3-substituted-1,2-dione I (shown as the enol) or the dihydrofuran derivative II:

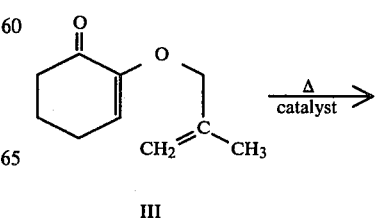

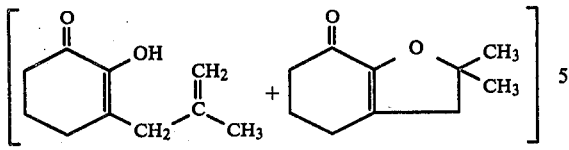

These intermediates are not isolated, but are further heated in the presence of an aromatization catalyst (such as palladium on various supports or sulfur) to yield the benzofuranol IV:

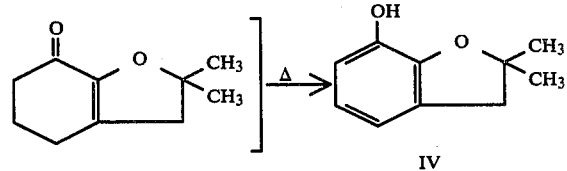

The benzofuranol IV is then converted to carbofuran by standard carbamoylation procedures, such as by reaction with methyl isocyanate in the presence of a tertiary amine catalyst:

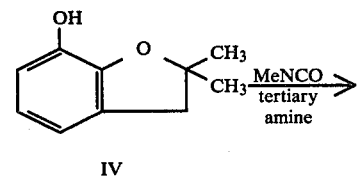

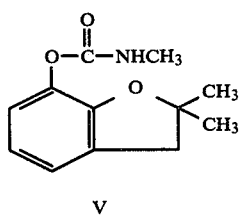

In addition to the diosphenol, another intermediate which is useful in the preparation of carbofuran is the corresponding ring-saturated derivative of III, 2-beta-methallyloxycyclohexanone VI. This compound can be prepared, as indicated in the examples, by the reaction of cyclohexene oxide and beta-methallyl alcohol followed by the oxidation of the cyclohexanol to the cyclohexanone:

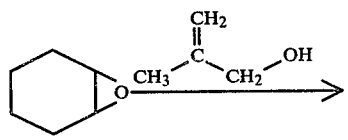

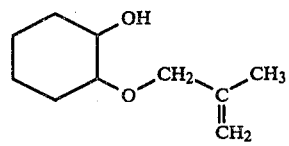

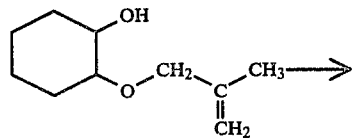

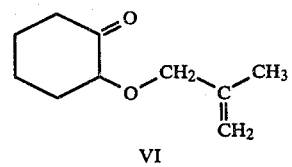

Aromatization and rearrangement of VI also results in the benzofuranol IV.

In practice, the process provides a simple, inexpensive route to carbofuran phenol and carbofuran itself. Moreover, the formation of hazardous intermediates is avoided and the method utilizes relatively inexpensive starting materials and simple chemistry.

As indicated above, the 2-beta-methallyloxy-2-cyclohexen-1-one (III), which is a novel compound, can undergo cyclization/aromatization to form the carbofuran phenol IV. Mechanistically, the beta-methallyloxy-2-cyclohexen-1-one can undergo the Claisen rearrangement to yield the diosphenol, aromatize, and cyclize onto oxygen or cyclize first to yield the dihydrofuran derivative II, followed by aromatization to yield the desired phenol.

As previously indicated, the first step in the process of this invention is the acid-catalyzed or base-catalyzed alkylation of cyclohexanedione at an oxygen or ring carbon atom. The technique is well known and disclosed in British Pat. No. 1,258,554 which issued Apr. 2, 1970 to Bayer A. G. and also reported by M. S. Gibson, J. Chem. Soc. (1962) 681. In the present invention beta-methallyl alcohol or a beta-methallyl halide, depending upon the catalyst used, is employed as the alkylating agent.

Reaction conditions and ratio of reactants are not necessarily critical and the process can be carried out under a variety of conditions.

A variety of acid and base alkylation catalysts can be used and the particular choice may depend upon economic reasons or other considerations. Catalysts which have been employed successfully in this invention include, among others, the acidic alkylation catalysts such as p-toluenesulfonic acid, boron trifluoride and the like.

In the second step, the diosphenol III undergoes the Claisen rearrangement and upon further heating in the presence of an aromatization catalyst, the intermediates formed undergo aromatization to the benzofuranol. The Claisen rearrangement of enol or phenol allyl ethers is known. Additionally, the Claisen rearrangement of 2-allyl-oxy-2-cyclohexen-1-one to yield the 3-allyl-1,2-cyclohexanedione has been reported in the literature. However, the cyclization/aromatization of the novel compound 2-beta-methallyloxy-2-cyclohexen-1-one was not heretofore known.

It has been observed that in the absence of an aromatization catalyst, that is conducting the second step by heating alone, only small amounts of the benzofuranol IV is formed. Accordingly, to obtain sufficient yields of the desired phenol compound the use of a catalyst is preferred.

Although palladium and sulfur were used in the examples, any catalyst which is known to effect aromatization and which would otherwise not adversely affect the reactants or product can be used. Illustrative of other catalysts which can be employed, include, but are not limited to copper, chromium, selenium, nickel, and platinum, and in general any noble metal catalyst and combinations thereof such as nickel-copper-chromite.

The temperatures employed in the second step are not necessarily critical and can vary over a wide range depending upon the reaction period. All that is necessary is that the desired rearrangement and aromatization be achieved.

In practice it has been found that temperatures of from about 150° C. to about 350° C., and preferably from about 150° C. and about 250° C. were satisfactory to effect the desired reaction. Temperatures above and below this range can be employed but are less preferred.

The reaction time in which to effect rearrangement and aromatization can vary. However, reaction periods of up to about 1-8 hours have been found to be satisfactory.

As indicated, once the benzofuranol (carbofuran phenol) is obtained it can be converted to carbofuran by standard carbamoylation procedures known in the art. By reacting benzofuranol with methylisocyanate in the presence of a tertiary amine catalyst, excellent yields of the desired carbofuran are obtained.

The following examples illustrate the best mode presently contemplated for the practice of this invention:

EXAMPLE 1

SYNTHESIS OF O- AND C-BETA-METHALLYL ALKYLATED 1,2-CYCLOHEXANEDIONE VIA BASE CATALYSIS

To a 500 ml 3-neck round bottom flask equipped with a magnetic stirrer, reflux condenser, $N_2$ inlet, and addition funnel were added, 1,2-cyclohexanedione (7.50 g; 67.00 mmol), acetone (250 ml), potassium carbonate (27.62 g; 200 mmol) and potassium iodide (20.00 g; 120 mmol). The reaction mixture was heated to reflux under $N_2$, and beta-methallyl chloride (18.10 g; 200 mmol) was added dropwise over a 15 minute period. The reaction mixture was refluxed with stirring under a $N_2$ blanket for 17 hours. The mixture was then allowed to cool to room temperature and was filtered in order to remove salts. The filtrate was concentrated (rotary evaporation) to yield 18.75 g of a light brown oil which was distilled in vacuo to give 6.79 g (61 percent) of the desired product as a pale yellow oil, bp 93°–98° C./5–6 torr. After distillation, 'H nmr analysis revealed a mixture of both O- and C-alkylated product. 'H nmr (CDCl$_3$): For O-alkylated product: $\delta$1.68–2.76 (m, 9, aliphatic —CH$_3$, —CH$_2$'s), 4.21 (s, 2, —O—CH$_2$), 4.83 (m, 2, vinylic —CH$_2$), 5.87 (t, 1, endocyclic olefinic —CH). For C-alkylated product: $\delta$1.68–2.76 (m, 9, aliphatic —CH$_3$, —CH$_2$ Lk 's), 3.02 (s, 2, exocyclic —CH$_2$), 4.78 (m, 2 vinylic —CH$_2$), 6.28 (bds, 1, —OH). IR (Film, of mixture): 910, 1140, 1200, 1225, 1390, 1665, 3440 cm$^{-1}$.

EXAMPLE 2

SYNTHESIS OF O-BETA-METHALLYL ALKYLATED 1,2-CYCLOHEXANEDIONE VIA ACID CATALYSIS

To a 500 ml round bottom flask equipped with an 18 inch Oldershaw column (10 trays), Dean-Stark trap, reflux condenser, heating mantle, and magnetic stirrer were added 1,2-cyclohexanedione (100.00 g; 893 mmol), benzene (125 ml), beta-methallyl alcohol (160 ml), and p-toulene-sulfonic acid (0.5 g). The mixture was then vigorously refluxed for 24 hours and water was collected. The mixture was permitted to cool, and 0.6 g CaCO$_3$ was added. The mixture was filtered and concentrated (rotary evaporation) to yield 146.27 g of a brown oil which was distilled in vacuo to give 114.86 g (77 percent) of a mixture of C-alkylated and cyclized product as a pale yellow oil, bp 122°–129.5° C./10–10.5 torr. 'H nmr (CDCl$_3$): For C-alkylated product: $\delta$0.89–2.67 (m, 9; aliphatic-CH$_3$, —CH$_2$'s), 3.02 (s, 2, exocyclic-CH$_2$), 4.78 (m, 2, vinylic-CH$_2$), 6.17 (bds, 1, OH). For cyclized product: $\delta$1.40 (s, 6, —CH$_3$'s), 1.85–2.63 (m, 8, —CH$_2$'s). IR (film): 880, 1380, 1665.

EXAMPLE 3

NON-CATALYTIC CLAISEN REARRANGEMENT/AROMATIZATION OF 2-BETA-METHALLOYLOXY-2-CYCLOHEXEN-1-ONE

To a 50 ml single neck round bottom flask equipped with a magnetic stirrer and $N_2$ inlet were added 2-beta-methallyl-oxy-2-cyclohexen-1-one (2.50 g; 15.54 mmol) and anhydrous MgCl$_2$ (0.2 g). The mixture was heated with stirring under a $N_2$ blanket at 184° C. for 6.5 hours. The mixture was allowed to cool and was distilled in vacuo to yield three fractions: (a) 2,2-dimethyl-2,3-dihydrobenzofuran, 0.55 g (23.91 percent yield), bp 49°–52° C./3.0 torr; 'Hnmr (CDCL$_3$): $\delta$1.44 (s, 6, gem-CH$_3$); 2.96 (s,2,benzylic-OCH$_2$: 6.80–7.23 (m,4,ArH); (b) an unidentified fraction containing mainly aliphatic material based on 'H nmr analysis, 0.22 g, bp 76°–90° C./3.0 torr; (c) a fraction containing some carbofuran phenol, 0.50 g, bp 92°–97° C./3.0 torr; 'H nmr (CDCl$_3$): $\delta$1.48 (s,6, gem-CH$_3$), 2.98 (s,2, benzylic-CH$_2$), 5.38 (bds, 1, —OH), 6.66 (s,3, ArH).

EXAMPLE 4

CATALYTIC CLAISEN REARRANGEMENT/AROMATIZATION OF 2-BETA-METHALLYLOXY-2-CYCLOHEXEN-1-ONE

2-Beta-Methallyloxy-2-cyclohexen-1-one (3.00 g; 18.1 mmol) and 60 mg of 0.3 percent Pd/alumina catalyst were placed into a 10 ml round bottom flask equipped with a magnetic stirrer, oil bath, and $N_2$ inlet. The mixture was heated at 150° C. for 6 hours under a $N_2$ blanket, at which point sulfur powder (0.53 g; 18.1 mmol) was added, and the mixture was heated an additional 5 hours at 185°–203° C. under a $N_2$ blanket. The mixture was allowed to cool and 'H nmr spectrum of the mixture was recorded. NMR analysis revealed that a significant amount of carbofuran phenol was present.

EXAMPLE 5

The carbofuran phenol from Examples 3 and 4 is then reacted with methyl isocyanate in the presence of a tertiary amine catalyst to give carbofuran (2,3-dihydro-2,2-dimethyl-7-benzofuranyl-N-methyl carbamate).

EXAMPLE 6
SYNTHESIS OF 2-BETA-METHALLYLOXY-CYCLOHEXANONE

A. Preparation of 2-beta-methallyloxycyclohexanol.

To a 250 ml round bottom flask equipped with a reflux condenser and magnetic stirrer were added cyclohexene oxide (25.00 g. 0.255 mol), beta-methallyl alcohol (100 ml), and stannous octoate (5 drops). The mixture was refluxed with stirring for 168 hours (7 days). The mixture was allowed to cool and excess alcohol removed via rotary evaporation to yield 38.97 grams of a water-white oil. 'Hnmr analysis was consistent with the structure of the desired product.

The above procedure was repeated using 37.52 g (0.383 mol) of cyclohexene oxide, 200 ml of beta-methallyl alcohol and 7 drops of the stannous octoate. The mixture was refluxed with stirring for 90 hours and then rotary evaporated to yield 32.99 gram of a water-soluble oil (50.67% yield). NMR and IR analysis were consistent with the structure of the desired product.

B. Preparation of 2-beta-methallyloxy cyclohexanone

To a 500 ml round bottom flask equipped with a magnetic stirrer, low temperature thermometer and two addition funnels were added $CH_2Cl_2$ (150 ml) and oxalyl chloride (9.65 g, 0.076 mol/6.0 ml). One addition funnel was charged with DMSO (11.08 g, 0.142 mol/11 ml) in $CH_2Cl_2$ (30 ml). The other addition funnel was charged with 2-beta-methallyloxycyclohexanol (11.10 g, 0.0653 mol) in $CH_2Cl_2$ (60 ml). The DMSO-$CH_2Cl_2$ mixture was added dropwise to the stirring oxyalyl chloride mixture at $-70°$ C. (gas). The mixture was then stirred for 10 minutes at $-65°$ C. The $CH_2Cl_2$/alcohol mixture was added over a 5 minute period (exotherm to $-60°$ C.). The resulting milky solution was then stirred for 15 minutes at $-60°$ C. Triethylamine (TEA) (42 ml) was added as rapidly as possible (exotherm to $-50°$ C.). The mixture was then stirred at $-55°$ C. for 5 min, followed by warming to room temperature. The mixture was then poured into 350 ml cold water. The organics were separated and the aqueous phase was extracted with 2×150 ml $CH_2Cl_2$. The organics were combined, and washed with 1% HCl until acidic. The organics were then washed with water (250 ml), 5% $Na_2CO_3$ (200 ml), and water (200 ml). The $CH_2Cl_2$ was then removed by rotary evaporation to yield 14.36 g of a yellow oil. Analysis of the oil showed it to be consistent with the structure of the desired product.

Although the invention has been illustrated by the preceding examples it is not to be construed as being limited to the materials employed therein, but rather the invention encompasses the generic area as hereinbefore disclosed. Various modifications and embodiments of the invention can be made without departing from the spirit and scope thereof.

What is claimed is:

1. A process for the preparation of 2,3-dihydro-2,2-dimethyl-7-benzofuranyl-N-methyl carbamate which comprises the steps of:
   (a) reacting 1,2-cyclohexanedione with a beta-methallyl alcohol or halide in the presence of alkylation catalyst to form 2-beta-methallyloxy-2-cyclohexen-1-one;
   (b) heating said 2-beta-methallyloxy-2-cyclohexen-1-one to a temperature sufficient to cause rearrangement and aromatization to 2,3-dihydro-2,2-dimethyl-7-benzofuranol; and
   (c) reacting said 2,3-dihydro-2,2-dimethyl-7-benzofuranol with methyl isocyanate to form said 2,3-dihydro-2,2-dimethyl-7-benzofuranyl-N-methyl carbamate.

2. The process of claim 1 wherein said alkylation catalyst is an acidic catalyst.

3. The process of claim 2 wherein said acidic catalyst is p-toluenesulfonic acid.

4. The process of claim 1 wherein said alkylation catalyst is a basic catalyst.

5. The process of claim 4 wherein said basic catalyst is potassium carbonate.

6. The process of claim 1 wherein said beta-methallyl halide is beta-methallyl chloride.

7. The process of claim 1 wherein step (b) is carried out in the presence of an aromatization catalyst.

8. The process of claim 7 wherein said aromatization catalyst is palladium.

9. The process of claim 7 wherein said aromatization catalyst is sulfur.

10. A process for the preparation of 2,3-dihydro-2,2-dimethyl-7-benzofuranol which comprises the steps of:
    (a) reacting 1,2-cyclohexanedione with a beta-methallyl alcohol or halide in the presence of an alkylation catalyst to form 2-beta-methallyloxy-2-cyclohexen-1-one; and
    (b) heating said 2-beta-methyallyloxy-2-cyclohexen-1-one to a temperature sufficient to cause rearrangement and aromatization to said 2,3-dihydro-2,2-dimethyl-7-benzofuranol.

11. The process of claim 10 wherein said alkylation catalyst is an acidic catalyst.

12. The process of claim 11 wherein said acidic catalyst is p-toluenesulfonic acid.

13. The process of claim 10 wherein said alkylation catalyst is a basic catalyst.

14. The process of claim 13 wherein said basic catalyst is potassium carbonate.

15. The process of claim 10 wherein said beta-methallyl halide is beta-methallyl chloride.

16. The process of claim 10 wherein step (b) is carried out in the presence of an aromatization catalyst.

17. The process of claim 16 wherein said aromatization catalyst is palladium.

18. The process of claim 16 wherein said aromatization catalyst is sulfur.

19. 2-beta-methallyloxy-2-cyclohexen-1-one.

* * * * *